United States Patent [19]

Takahashi et al.

[11] Patent Number: 4,996,356
[45] Date of Patent: Feb. 26, 1991

[54] CARBOXYLIC ACIDS AND METHODS OF PREPARING THE SAME

[75] Inventors: Hiroshi Takahashi, Uji; Atushi Ohta, Kyoto; Sayumi Akasaki, Uji, all of Japan

[73] Assignee: Sanyo Chemical Industries, Ltd., Kyoto, Japan

[21] Appl. No.: 190,851

[22] Filed: May 6, 1988

[30] Foreign Application Priority Data

May 13, 1987 [JP] Japan .................. 62-116399
May 13, 1987 [JP] Japan .................. 62-116400

[51] Int. Cl.$^5$ ............................ C07C 59/10
[52] U.S. Cl. ..................... 562/587; 562/583; 260/410
[58] Field of Search ............ 562/587; 562/583; 260/410

[56] References Cited

U.S. PATENT DOCUMENTS 3,983,171  9/1976  Vanlerberghe et al. ............ 260/535

FOREIGN PATENT DOCUMENTS 2332539   1/1975  Fed. Rep. of Germany .
57-162797 10/1982  Japan .
2088863A  6/1982  United Kingdom .
2176783A  5/1986  United Kingdom .

OTHER PUBLICATIONS

Journal of the Chemical Society of Japan, vol. 9, 1980, pp. 1389–1390.

*Primary Examiner*—Paul J. Killos
*Attorney, Agent, or Firm*—Armstrong, Nikaido, Marmelstein, Kubovcik & Murray

[57] ABSTRACT

Biodegradable and little skin-roughening carboxylic acids being an excellent surfactant in a wide pH range and having the general formula (1):

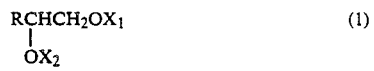

wherein R is a linear or branched alkyl or alkenyl group containing from 4 to 34 carbon atoms; one or both of $X_1$ and $X_2$ are $-(CH_2)_n-COOM$, any other is a hydrogen atom; M is a hydrogen atom, an alkali metal, an alkaline earth metal, ammonium, a lower alkanol amine cation, a lower alkyl-amine cation or a basic amino acid cation; and n is 1 or 2; and simple methods of preparing the same.

3 Claims, 2 Drawing Sheets

FIG. I

CARBOXYLIC ACIDS AND METHODS OF PREPARING THE SAME

FIELD OF THE INVENTION

The present invention relates to new carboxylic acids. More particularly it relates to carboxylic acids useful as surfactants and methods of preparing the same.

BACKGROUND OF THE INVENTION

Sodium polyoxyethylene alkyl ether carboxylates and o-substituted glyceric acid sodium salts have been known as surfactants of ether carboxylate type [The Chemical Society of Japan 1980, No. 9, 1385–1389; Japan Laying-open Patent 1982-162.797; etc.]. However, the former does not have sufficient properties as surfactant in areas of weak acid and alkali, though it exhibits good properties in neutral and weak alkaline areas. The latter has a defect of being too expensive due to its complicated method to prepare.

SUMMARY OF THE INVENTION

A principal object of this invention is to obtain new inexpensive surfactants having good properties in a wide pH range of from weak acid to alkali and being prepared by simple methods.

A further object of the invention is to provide methods of preparing carboxylic acids represented by the general formula (1) using 1,2-epoxyalkanes and 1,2-alkanediols as starting materials.

A further object of the invention is to provide carboxylic acids with a good surface activity and an excellent biodegradability.

A still further object of the invention is to provide carboxylic acids which are safe for living bodies and less irritant to the skin, besides being highly resistant to hard water.

DETAILED DESCRIPTION OF THE INVENTION

Figure 1:
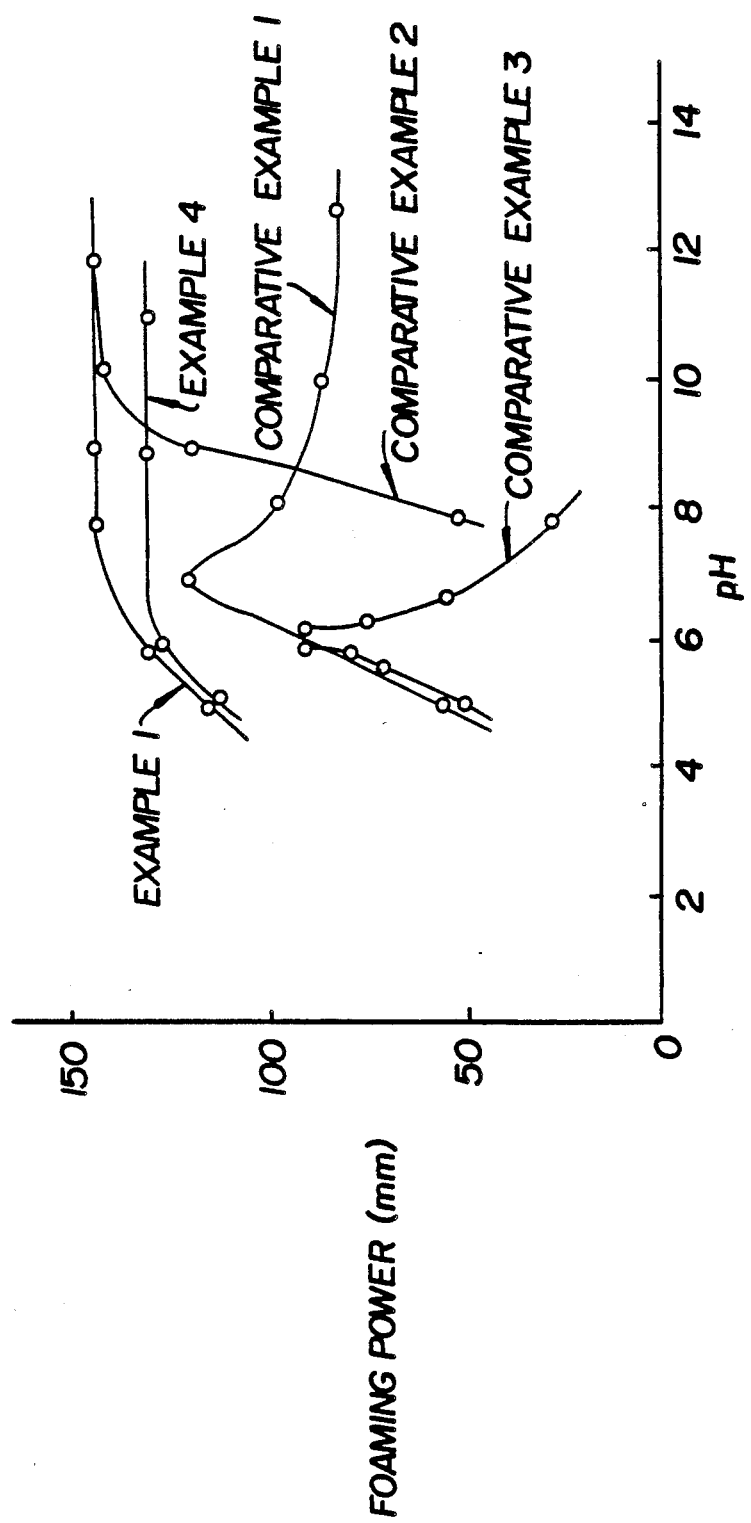

This invention provides carboxylic acids having the general formula (1):

wherein R is a linear or branched alkyl or alkenyl group containing from 4 to 34 carbon atoms; one of X and $X_2$ is $-(CH_2)_n-COOM$ and the other is a hydrogen atom; M is a hydrogen atom, an alkali metal, an alkaline earth metal, ammonium, a lower alkanol amine cation, a lower alkyl-amine cation or a basic amino acid cation; and n is 1 or 2; mixtures thereof with dicarboxylic acids of the same general formula; and methods of producing the same.

Suitable linear or branched alkyl groups containing from 4 to 34 carbon atoms which are represented by R in the general formula (1) include, for example, butyl, octyl, decyl, dodecyl, tetradecyl, hexadecyl, octadecyl, docosyl, 2-ethylhexyl, 2-hexyldecyl and 2-octhylundecyl groups. Suitable linear or branched alkenyl groups containing from 4 to 34 carbon atoms which are represented by R in the general formula (1) include, for example, decenyl, dodecenyl, tetradecenyl, hexadecenyl and octadecenyl groups. Among them, linear alkyl groups containing from 8 to 16 carbon atoms are preferred for their better surface actibities, decyl and dodecyl groups are particularly preferred. These alkyl or alkenyl groups may be one of mixtures of more than two groups.

Suitable alkali metals represented by M in the general formula (1) include, for example, sodium, potassium and lithium, Suitable alkaline-earth metals include, for example, calcium, magnesium and barium. Suitable alkanol amines which form lower alkanolamine cations include, for example, mono-, di- and tri-ethanol amine, and n- and isopropanol amine. Suitable alkyl amines which form lower alkylamine cations include, for example, monoethylamine, diethylamine and triethylamine. Suitable basic amino acids which form basic amino acid cations include, for example, lysine, arginine, ornithine and histidine. Among the materials represented by M, alkali metals and lower alkanol amines, particularly sodium and lower alkanol amine cations, are preferred. These may be one of mixtures of more than two ionizable substances.

Mixtures of the carboxylic acids represented by the general formula (1) contain monocarboxylic acids represented by the following general formula (1') and dicarboxylic acids represented by the general formula (1"):

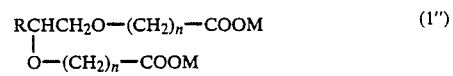

wherein one of $X_3$ and $X_4$ is a $-(CH_2)_n-COOM$ and the other is a hydrogen atom, R, M and n are the same as in the general formula (1).

Examples of the compounds and mixtures thereof represented by the general formula (1) are shown in Table 1 below.

TABLE 1

| Compound No. | R | $X_1$ | $X_2$ | M |
|---|---|---|---|---|
| 1 | C10 | H | $-CH_2CH_2COOM$ | H |
| 2 | C10 | $-CH_2CH_2COOM$ | H | H |
| 3 | C12 | H | $-CH_2CH_2COOM$ | H |
| 4 | C12 | $-CH_2CH_2COOM$ | H | H |
| 5 | | mixture of Compound 1 and 2 | | |
| 6 | | mixture of Compound 3 and 4 | | |
| 7 | C10 | $-CH_2CH_2COOM$ | H | Na |
| 8 | C10 | H | $-CH_2CH_2COOM$ | Na |
| 9 | | mixture of Compound 7 and 8 | | |
| 10 | C10 | | $-CH_2CH_2COOM$ | Na |
| 11 | C12 | | $-CH_2CH_2COOM$ | Na |
| 12 | C14 | | $-CH_2CH_2COOM$ | Na |
| 13 | C10 | | $-CH_2CH_2COOM$ | Na/H |
| 14 | C10 | | $-CH_2CH_2COOM$ | H |
| 15 | C10 | | $-CH_2CH_2COOM$ | TEA |
| 16 | C12 | | $-CH_2CH_2COOM$ | H |
| 17 | | mixture of Compound 9 (70 wt. %) and 10 (30 wt. %) | | |
| 101 | C10 | H | $-CH_2COOM$ | Na |
| 102 | C10 | $-CH_2COOM$ | H | Na |
| 103 | C12 | H | $-CH_2COOM$ | Na |
| 104 | C12 | $-CH_2COOM$ | H | Na |
| 105 | | mixture of Compound 101 and 102 | | |
| 106 | | mixture of Compound 103 and 104 | | |
| 107 | C10 | $-CH_2COOM$ | H | TEA |
| 108 | C12 | $-CH_2COOM$ | H | TEA |

TABLE 1-continued

| Compound No. | R | $X_1$ | $X_2$ | M |
|---|---|---|---|---|
| 109 | C8 | | —CH$_2$COOM | Na |
| 110 | C10 | | —CH$_2$COOM | Na |
| 111 | C12 | | —CH$_2$COOM | Na |
| 112 | C14 | | —CH$_2$COOM | Na |
| 113 | C10 | | —CH$_2$COOM | Na/H |
| 114 | C10 | | —CH$_2$COOM | H |
| 115 | C10 | | —CH$_2$COOM | TEA |
| 116 | | mixture of Compound 105 (70 wt. %) and 110 (30 wt. %) | | |

The alphanumerical codes used in Table 1 correspond to the following radicals or substances respectively:

| | |
|---|---|
| C8 | n-C$_8$H$_{17}$ |
| C10 | n-C$_{10}$H$_{21}$ |
| C12 | n-C$_{12}$H$_{25}$ |
| C14 | n-C$_{14}$H$_{29}$ |
| TEA | NH(CH$_2$CH$_2$OH)$_3$ |
| Na/H | Na/H (50/50) |

The carboxylic acids of this invention can be manufactured by reacting 1,2-alkanediols represented by the general formula (2) with acrylonitrile, acrylic acid or acrylic acid lower alkyl esters and, if necessary, hydrolyzing the reaction product (a).—The first invention.

The carboxylic acids may also be prepared by reacting alkoxides [general formula (2-1)]of said 1,2-alkanediols with monohaloacetic acids or their salts and, if necessary, converting the reaction product into the corresponding free acids or salts. —The second invention.

When acrylonitrile is employed, the reaction can be illustrated as follows:

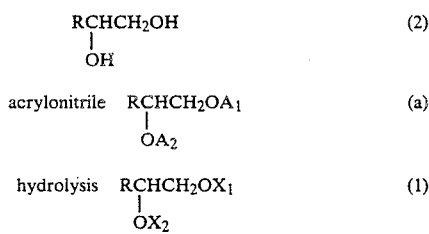

wherein one or both of $A_1$ and $A_2$ are —CH$_2$CH$_2$CN and any other is a hydrogen atom, and R, $X_1$ and $X_2$ are the same as defined in the general formula (1).

When a monohaloacetic acid (or its salt) is used, the reaction will proceed as follows:

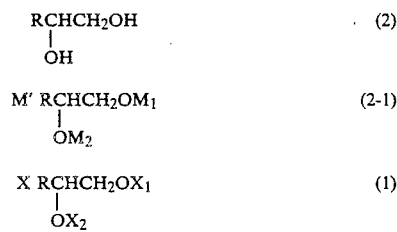

wherein M' is an alkali metal; one or both of $M_1$ and $M_2$ are alkali metals and any other is a hydrogen atom; X is a monohaloacetic acid or its salt; and R, $X_1$ and $X_2$ are the same as defined in the general formula (1).

Suitable acrylic acid lower alkyl esters to be used in the reaction with the 1,2-alkanediol include, for example, methyl acrylate, ethyl acrylate, propyl acrylate and butyl acrylate. Methyl acrylate and ethyl acrylate are preferred for their good reactivity and easiness in handling.

If necessary, the reaction of the 1,2-alkanediol (for example, 1,2-dodecanediol or 1,2-tetradecanediol) [general formula (2)]with acrylonitrile, acrylic acid or the acrylic acid lower alkyl ester can be carried out in a suitable solvent and/or in the presence of a catalyst.

Suitable solvents used in case of necessity include, for example, dimethyl formamide, dioxane, tetrahydrofuran and hexane.

Suitable catalysts used in case of necessity include alkali metal hydroxides such as lithium hydroxide, sodium hydroxide and potassium hydroxide; alkoxides such as sodium methylate and sodium ethylate; and metallic sodium and metallic pottasium. Sodium methylate is particularly preferred for its high activity.

In the said reaction, polymerization inhibitors such as hydroquinone and hydroquinone monomethyl ether may be employed in a small amount to avoid polymerization of acrylonitrile or acrylic acid derivatives.

Acrylonitrile, acrylic acid or the acrylic acid lower alkylester is generally used in the reaction in an amount to provide from 0.5 to 4.0 moles, preferably from 0.9 to 2.4 moles, per mole of the 1,2-alkanediol.

The catalist is generally used in an amount to provide from 0 to 10 molar percent preferably from 0.1 to 2 molar percent, for the 1,2-alkanediol.

The said reaction is generally carried out at a temperature of from 0 to 80° C. for 1 to 8 hours, but it may be conducted beyond these temperature and time ranges according to the combination of starting materials.

The reactaning product thus obtained (a) is then hydrolyzed, in case of acrylonitrile or acrylate being reacted, with an acid (hydrochloric acid or sulfuric acid) or an alkali (sodium hydroxide or potassium hydroxide) to obtain the carboxylic acids represented by the general formula (1).

In case of a process in which the monohaloacetic acid (or its salt) being employed, the 1,2-alkanediol (1,2dodecanediol, 1,2-tetradecanediol or the like) is alcoholated in a solvent in the presence of alkali, then the resulting alkoxide [general formula (2-1)]is carboxymethylated by the adding the monohaloacetic acid or its salt.

Suitable solvents employed in the reaction include, for example, solvents such as dioxane, diethylene glycol dimethyl ether, hexane, toluol and water; the 1,2-alkanediol [general formula (2)]; and mixtures thereof.

Suitable alkalis which provide the alkoxide (2-1) include, for example, metallic sodium, liquid methylate, sodium hydroxide and potassoium hydroxide; preferably metallic sodium, liquid methylate and sodium hydroxide.

As a monohaloacetic acid or a salt thereof, monochloracetic acid or its sodium salt is preferred for economical reason.

The alkali to provide the alkoxide [general formula (2-1)] is generally employed in an amount of from 0.2 to 6.0 moles, preferably from 0.5 to 3.0 moles, per mole of the monohaloacetic acid or its salt. The monohaloacetic acid or its salt is generally employed in an amount to provide more than molar equivalent, preferably from 0.9 to 3.0 molar equivalents, for the said alcoholate.

Temperatures at which the alcoholation and the carboxymethylation are carried out generally range from 10° C. to the boiling point of the solvent used, preferably from 30 to 100° C.. At temperatures below 10° C., these reactions do not proceed satisfactorily.

Addition of the monohaloacetic acid or its salt to the reaction system may be optionally made in either way, at one time or in parts.

The carboxylic acids of the present invention can also be prepared by carboxymethylation of the ester of a 1,2-epoxyalkane represented by the general formula (3):

wherein R is a linear or branched alkyl or alkenyl group having from 4 to 34 carbon atoms, in a solvent with the monohaloacetic acid and/or its salts in the presence of alkali.

The reaction can be illustrated as follows:

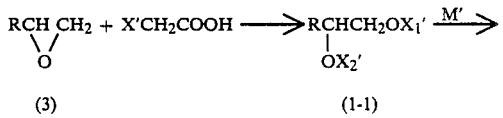

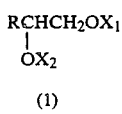

wherein X′ is a halogen atom; one or both of $X_1'$ and $X_2'$ are —$COCH_2X$, any other is a hydrogen atom; R is the same as in the formula (3); one or both of $X_1$ and $X_2$ are —$CH_2COOM$, any other is a hydrogen atom; M is the same as in the formula (1) and M′ is an alkali metal hydroxide.

Suitable solvents used in the reaction include, for example, a solvent such as dioxane, diethyleneglycol dimethyether, hexane, toluol and water; and a mixture thereof.

Suitable alkali metal hydroxides used in the reaction include, for example, lithium hydroxide, sodium hydroxide and potassium hydrooxide.

As the monohaloacetic acid and/or its salt, monochloracetic acid and/or its salt are preferred for economical reason.

The monohaloacetic acid and/or its salt to provide the ester [general formula (1-1)]are used in a quantity of from 0.2 to 20 moles, preferably from 0.5 to 10 mols, per mole of the 1,2-epoxyalkane. The weight ratio of the monohaloacetic acid to its salt is within the range of 100:0 to 40:60 in general, preferably 98:2 to 60:40.

The alkali metal hydroxide for carboxymethylation is employed in a quantity of from 0.5 to 5.0 moles in general, preferably from 0.8 to 2.0 moles, per mole of the monohaloacetic and/or its salt used.

The esterification temperature is generally in the range of from 10 to 150° C., preferably from 30 to 100° C. The lower the temperature is, the less the reactivity will be; the higher the temperature is, the more by-products and coloring will be.

The carboxymethylation is generally carried out at a temperature of from 10° C. to the boiling point of the solvent used, preferably from 30 to 100° C. At a temperature below 10° C., the reaction does not proceed satisfactorily.

Moreover, the carboxylic acids of the present invention can also be prepared by hydrolyzing a reaction product between the 1,2-epoxyalkane represented by the general formula (3) and ethylene cyanohydrin into a carboxylic acid or a salt.

wherein R is a linear or branched alkyl or alkenyl group having from 4 to 34 carbon atoms. —The third invention.

If necessary, the reaction of the 1,2-epoxyalkane [general formula (3); 1,2-epoxydodecane, 1,2-epoxytetradecane of the like]with ethylene cyanohydrin may be carried out in the presence of an alkaline catalyst, such as sodium hydroxide, potassium hydroxide or triethyamine, or an acid catalyst such as sulfuric acid or trifluoroboron.

When products of this reaction are hydrolyzed with an acid (hydrochloric acid or sulfuric acid) or an alkali (sodium hydroxide or potassium hydroxide), the carboxylic acids represented by the general formula (1) are given.

Furthermore, the carboxylic acids of the present invention can also be prepared by hydrolyzing a reaction product of the 1,2-epoxyalkane [general formula (3)]with an alkyl glycolate represented by the general formula (4) into the corresponding acid or salt. —The fourth invention.

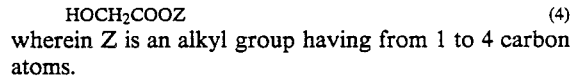

wherein Z is an alkyl group having from 1 to 4 carbon atoms.

The reaction of the 1,2-epoxyalkane [general formula (3)]with the alkyl glycolate represented by the general formula (4) (methyl glycolate, ethyl glycolate, or the like) may be carried out, if necessary, in the presence of an alkaline catalyst such as sodium hydroxide, potassium hydroxide or triethyamine, or an acid catalyst such as sulfuric acid or trifluoroboron.

Unreacted materials and by-products contained in a reaction product are removed by column chromatography or liquid chromatography, so that the acids (salts) of this invention can be obtained in purified form.

To convert the resulting salt into a more preferable salt type, the said salt is acidified with a mineral acid such as sulfuric acid or hydrochloric acid, after which it is solvent-extracted using petroleum ether, diethyl ether or hexane, and then neutralized with a desired base.

Of the carboxylic acids of the present invention, monocarboxylic acids represented by the general formula (1′) exhibit better properties as surfactant than dicarboxylic acids represented by the general formula (1″), and mixtures of the two containing a sufficient amount of the monocarboxylic acids (more than 20%, particularly more than 50%) are also useful for their high foaming power.

Products obtained by the method of the second invention are ordinarily mixtures of the monocarboxylic acids given by the formula (1′) and dicarboxylic acids given by the formula (1″). These mixtures may be isolated to each other. But in industrial uses, it is preferred to use the mixtures as they are. The weight ratio of the monocarboxylic acids to the dicarboxylic acids is generally within the range of 9:1 to 2:8, preferably 8:2 to 5:5. Such preferable ratio can be obtained by the method of either the third invention or the fourth invention.

The compounds and the methods of preparing the same provided by the present invention have many advantages as described below.

(1) The compounds provided by the invention exhibit an excellent foaming power in a wide pH range from weak acid to alkali. When ordinary ether carboxylates (Comparative Example 1, for instance) are taken for comparison, their foaming power is not as good as that of the compounds based on the present invention, particularly in weak acid and alkaline areas. Soaps (Comparative Example 2, for instance) exhibit excellent foaming power in an alkaline area, but they cannot be used in weak acid and neutral areas. Alkyl (or alkenyl) succinates (Comparative Example 3, for instance) are also insufficient in foaming power.

(2) The compounds of the present invention can be easily prepared. Though ortho-substituted glycerinates have good properties, preparation of these materials needs a complicated oxidation process which makes them very expensive.

(3) The compounds of the invention exhibit an great capability of reducing surface tension and are useful as surfactants.

(4) The compounds of the invention have an excellent solubility in a wide pH range. Solubilities of ordinary ether carboxylates (Comparative Example 1, for instance) and alkyl (or alkenyl) succinates (Comparative Example 3, for instance) are poor in a pH ranging from weak acid to acid. Soaps (Comparative Example 2, for instance) are hardly soluble in water in a pH range of from neutral to acid.

(5) The compounds provided by the invention exhibit excellent resistance to hard water, while a soap solution (for example, Comparative Example 2) become turbid when mixed with hard water.

(6) The compounds provided by the invention are biodegradable and substantially free from fear of environmental pollution.

(7) The compounds provided by the invention are very mild to the skin and safe for living bodies.

(8) The compounds provided by the invention have excellent properties of emulsifying oils and dispersing inorganic perticles like soil, besides a good penetrability to cloths.

(9) The compounds provided by the invention show a good detergency against oily stains like sebum and inorganic stains like soil.

(10) The compounds provided by the invention withstand hydrolysis to a large extent and can be used in an alkaline solution.

With these advantages the compounds of the present invention can be favorably utilized in areas of body shampoos, skin detergents like cleansing agents, hair detergents like shampoos and household detergents like dish washing detergents. In addition to these toilet and household uses, the compounds can also be advantageously used in industries making medicines, agricultural chemicals, textiles, machinery, plastic & rubber goods, petreum, paper & pulp, paints and many others; as detergents, foaming agents, penetrating agents, emulsifying agents, solubilizing agents, dispersants, smoothing agents, lubricants, antistatic agents and rust inhibitors.

The following examples are illustrative of the present invention but are not to be construed as to limiting the scope thereof in any manner.

EXAMPLE 1

Into a 500 ml. four-necked flask were weighed 50.0 g. of 1,2-dodecanediol, 100 g. of dimethyl formamide and 0.45 g. of liquid methylate (28% methanol solution), the mixture was thoroughly dissolved at a temperature below 50° C. under a stream of nitrogen, and the solution was cooled to 20° C. Then 13.8 g. of acrylonitrile was added dropwise at a rate to maintain the temperature of the solution between 20°–30° C. When the addition was complete the reaction was continued for further 2 hours keeping the temperature at 20°–30° C. After completion of the reaction, the catalyst was neutralized with an addition of 0.27 g. of hydrochloric acid (36% aqueous solution), the solvent was then distilled off at a temperature below 100° C. under reduced pressure. The reactant was then hydrolyzed, with an addition of 62.9 g. of hydrochloric acid (36% aqueous solution), at 85° C. for 6 hours to obtain Compound 5 given in Table 1. The resulting hydrolyzate (cruden yield : 90%) was thoroughly washed with water to remove the excess hydrochloric acid, then unreacted materials and by-products were separated by preparative liquid chromatography under the following conditions:

| Silica gel column (Wakogel C-200) | |
| --- | --- |
| eluent | chloroform/methanol = 5/5 → chloroform/ethylacetate = 7/3 |

Thus, 19.0 g. of purified Compound 5 having the following analyses was obtained.

Elemental analysis (unit : %)

| | Measured value | Calculated value |
| --- | --- | --- |
| C | 65.8 | 65.7 |
| H | 11.0 | 10.9 |
| O | 23.2 | 23.4 |

NMR(CDCl$_3$)δ0.87 (bt, 3H), 1.28 (bs, 18H), 2.62 (bt, 2H) 3 22–3.58 (ddd, 2H), 3.62–3.87 (m, 3H)

IR (KBr) : cm$^{-1}$ 3430, 2955, 2925, 2850, 1710, 1470, 1440, 1330, 1230, 1190, 1130, 1115.

Acid value (mg.KOH/g.) : 203.9 (calculated value : 204.7)

EXAMPLE 2

Into a 500 ml. four-necked flask were weighed 50.0 g. of 1,2-tetradecanediol, 100 g. of dimethylformamide and 0.45 g. of liquid methylate (28% methanol:solution), the mixture was thoroughly dissolved below 50° C. under a nitrogen stream, and the solution was cooled to 20° C. Then 11.5 g. of acrylonitrile was added dropwise at a rate to maintain the temperature of the solution between 20 to 30° C. After completion of the addition, the reaction was continued for further 2 hours keeping the temperature at 20 to 30° C. When the reaction was complete, the catalyst was neutralized with an addition of 0.27 g. of hydrochloric acid (36% aqueous solution), the solvent was then distilled off at a temperature below 100° C. under reduced pressure. The reactant was then hydrolyzed, with an addition of 62.9 g. of hydrochloric acid (36% aqueous solution), for 6 hours at 85° C. to obtain Compound 6 shown in Table 1. The resultant hydrolyzate (crude yield : 88%) was thoroughly washed with water to remove the excess hydrochloric acid, then unreacted materials and by-products contained therein were separated by column chromatography under the same conditions as described in Example 1. Thus, 18.5 g. of purified Compound 6 having the following analyses was obtained.

Elemental analysis (unit : %)

|   | Measured value | Calculated value |
|---|---|---|
| C | 67.3 | 67.5 |
| H | 11.4 | 11.3 |
| O | 21.3 | 21.2 |

MMR (CDCl$_3$) : δ0.87 (bt, 3H), 1.27 (bs, 22H), 2.61 (bt, 2H) 3.21–3.60 (ddd, 2H), 3.64–3.88 (m, 3H)

IR (KBr) : cm$^{-1}$ 3450, 2955, 2925, 2875, 2855, 1710, 1465, 1440, 1330, 1230, 1190, 1130, 1115.

Acid value (mg.KOH/g.) : 185.0 (calculated value : 185.8)

EXAMPLE 3

5.0 g. of the hydroxyether monocarboxylic acid obtained in Example 1 was dissolved in 30 g. of ethanol and then neutralized with 0.73 g. (equivalent to the amount of the acid used) of sodium hydroxide. When the ethanol was removed, 4.5 g. of sodium hydroxyether monocarboxylate was obtained.

Elemental analysis (unit : %)

|   | Measured value | Calculated value |
|---|---|---|
| C | 60.7 | 60.8 |
| H | 9.7 | 9.8 |
| O | 21.6 | 21.6 |
| Na | 8.0 | 7.8 |

Weak acid value (mg.KOH/g: 188.9 (calculated value : 189.5)

CMC (mol./l.) : $4.5 \times 10^{-4}$

EXAMPLE 4

Into a 500 ml. four-necked flask were weighed 50.0 g. of 1,2-dodecanediol, 100 g. of dimethylformamide and 0.45 g. of liquid methylate (28% methanol solution), the mixture was thoroughly dissolved below 50° C. under a nitrogen stream, and the solution was cooled to 20° C. Then 27.6 g. of acrylonitrile was added dropwise at a rate to maintain the temperature of the solution between 20 to 30° C. After completion of the addition, the reaction was continued for further 2 hours keeping the temperature at 20 to 30° C. When the reaction was complete, the catalyst was neutralized with an addition of 0.27 g. of hydrochloric acid (36% aqueous solution), the solvent was then distilled off at a temperature below 100° C. under reduced pressure. The reactant was then hydrolyzed, with an addition of 125.8 g. of hydrochloric acid (36% aqueous solution), for 6 hours at 85° C. to obtain Compound 14 shown in Table 1. The resultant hydrolyzate (crude yield : 90%) was thoroughly washed with water to remove the excess hydrochloric acid, then unreacted materials and by-products contained therein were separated by preparative liquid chromatography. Thus, 20,5 g. of purified Compound 14 having the following analyses was obtained.

Elemental analysis (unit : %)

|   | Measured value | Calculated value |
|---|---|---|
| C | 62.5 | 62.4 |
| H | 9.7 | 9.8 |
| O | 27.7 | 27.7 |

NMR(CDCl) : δ87 (bt, 3H), 1.24 (bs, 18H), 2.60 (bt, 4H) 3.36–3.55 (m, 3H), 3.60–3.90 (m, 4H)

IR (neat) : cm$^{-1}$ 3430, 2955, 2925, 2850, 1720, 1470, 1430, 1350, 1270, 1190, 1115, 1070, 720.

Acid value (mg.KOH/g.) : 324.9 (calculated value : 324.3)

EXAMPLE 5

Into a 500 ml. four-necked flask were weighed 50.0 g. of 1,2-tetradecanediol, 100 g. of dimethyl formamide and 0.45 g. of liquid methylate (28% methanol solution), the mixture was thoroughly dissolved below 50° C. under a nitrogen stream, and the solution was cooled to 20° C. Then 23.0 g. of acrylonitrile was added dropwise at a rate to maintain the temperature of the solution between 20 to 30° C. After completion of the addition, the reaction was continued for further 2 hours keeping the temperature at 20 to 30° C. When the reaction was complete, the catalyst was neutralized with an addition of 0.27 g. of hydrochloric acid (36% aqueous solution), the solvent was then distilled off at a temperature below 100° C. under reduced pressure. The reactant was then hydrolyzed, with an addition of 62.9 g. of hydrochloric acid (36% aqueous solution), for 6 hours at 85° C. to obtain Compound 16 shown in Table 1. The resultant hydrolyzate (crude yield : 90%) was thoroughly washed with water to remove the excess hydrochloric acid, then unreacted materials and by-products contained therein were separated by preparative liquid chromatography under the same conditions as described in Example 1. Thus, 19.0 g. of purified Compound 16 having the following analyses was obtained.

Elemental analysis (unit : %)

|   | Measured value | Calculated value |
|---|---|---|
| C | 64.1 | 64.2 |
| H | 10.1 | 10.2 |
| O | 25.7 | 25.7 |

NMR (CDCl$_3$) : δ0.86 (bt, 3H), 1.24 (bs, 22H), 2.60 (bt, 4H) 3.35–3.56 (m. 3H), 3.60–3.90 (m, 4H)

IR (neat) : cm$^{-1}$ 3450, 2955, 2925, 2875, 2855, 1710, 1465, 1440, 1330, 1230, 1190, 1130, 1115.

Acid value (mg.KOH/g.) : 299.2 (calculated value : 300)

EXAMPLE 6

5.0 g. of the diether monocarboxylic acid obtained in Example 4 was dissolved in 30 g. of ethanol and then neutralized with 1.2 g. (equivalent to the amount of the acid) of sodium hydroxide. By removing the ethanol, 5.6 g. of sodium diether carboxylate having the following analyses was obtained.

Elemental analysis (unit : %)

|   | Measured value | Calculated value |
|---|---|---|
| C | 55.2 | 55.4 |
| H | 8.3 | 8.2 |
| O | 24.7 | 24.6 |

|   | Measured value | Calculated value |
| --- | --- | --- |
| Na | 11.9 | 11.8 |

Weak acid value (mg.KOH/g.) : 288.0 (calculated value : 287.7)

CMC (mol./l.) : $5.5 \times 10^{-3}$

EXAMPLE A

Into a 1 liter four-necked flask were weighed 50.0 g. of 1,2-dodecanediol, 250 g. of dioxane and 5.7 g. of metallic sodium, and the mixture was heated to 100° C. under a nitrogen atmosphere. The mixture was stirred and maintained at 100° C. for 5 hours to complete the alkoxidation, then cooled to 70° C. Then 28.8 g. of sodium monochloroacetate was gradually added thereto. After completion of the addition, the reaction was continued at 70° C. for 3 hours to obtain Compound 105 shown in Table 1. The reaction product (crude yield : 80%) was then purified by distilling off the solvent and by subsequent preparative liquid chromatography conducted under the following conditions to remove unreacted materials and by-products:

Silica gel column (Wakogel C-200)

Eluent chloroform/methanol = 10/1 →methanol 20.5 g. of purified Compound 105 having the following analyses was thus obtained.

Elemental analysis (unit : %)

|   | Measured value | Calculated value |
| --- | --- | --- |
| C | 59.8 | 59.6 |
| H | 9.6 | 9.6 |
| O | 22.5 | 22.7 |
| Na | 8.1 | 8.2 |

MMR ($D_2O$) : δ0.86 (bt, 3H), 1.28 (bs, 18H), 3.28–3.61 (m, 2H), 3.70–4.10 (m, 3H)

IR (KBr) : $cm^{-1}$ 3370, 2960, 2925, 2875, 2855, 1600, 1465, 1455, 1425, 1375, 1325, 1115, 1100, 720

Weak acid value (mg.KOH/g.) : 199.5 (calculated value : 198.8)

CMC (mol./l.) : $3.1 \times 10^{-4}$

EXAMPLE B

Into a 1 liter four-necked flask were weighed 50.0 g. of 1,2-tetradecanediol, 250 g. of dioxane and 5.0 g. of metallic sodium, and the mixture was heated to 100° C. under a nitrogen atmosphere. The mixture was stirred and maintained at 100° C. for 5 hours to complete the alkoxidation, then cooled to 70° C. Then 27.8 g. of sodium monochloroacetate was gradually added thereto. After completion of the addition, the reaction was continued at 70° C. for 3 hours to obtain Compound 106 shown in Table 1. The reaction product (crude yield : 78%) was then purified by distilling off the solvent and by subsequent preparative liquid chromatography conducted under the same conditions as described in Example A to remove unreacted materials and by-products. Thus 19.8 g. of purified Compound 106 having the following analyses was obtained.

Elemental analysis (unit : %)

|   | Measured value | Calculated value |
| --- | --- | --- |
| C | 62.2 | 62.0 |
| H | 9.9 | 10.0 |
| O | 20.4 | 20.6 |
| Na | 7.5 | 7.4 |

MMR ($D_2O$) : δ0.87 (bt, 3H), 1.27 (bs, 22H), 3.25–3.60 (m, 2H), 3.70–4.08 (m, 3H)

IR (KBr) : $cm^{-1}$ 3350, 2960, 2925, 2875, 2855, 1610, 1465, 1455, 1425, 1375, 1325, 1115, 720

Acid value (mg.KOH/g.) : 180.0 (calculated value : 180.9)

EXAMPLE C 5.0 g. of the sodium hydroxyether monocarboxylate obtained in Example A was dissolved in 50 g. of water. After acidifying the solution with hydrochloric acid, the solute was extracted with ether. Thus 4.5 g. of the purified hydroxyether monocarboxylic acid having the following analyses was Elemental analysis (unit : %)

|   | Measured value | Calculated value |
| --- | --- | --- |
| C | 64.4 | 64.6 |
| H | 10.8 | 10.8 |
| O | 24.8 | 24.6 |

Acid value (mg.KOH/g.) : 216.0 (calculated value : 215.7)

Melting point (°C) 45.3

EXAMPLE D

Into a 1 liter four-necked flask were weighed 50.0 g. of 1,2-dodecanediol, 250 g. of dioxane and 11.4 g. of metallic sodium, and the mixture was heated to 100° C. under a nitrogen atmosphere. The mixture was stirred and maintained at 100° C. for 5 hours to complete the alkoxidation, then cooled to 70° C. Then 57.7 g. of sodium monochloroacetate was gradually added thereto. After completion of the addition, the reaction was continued at 70° C. for 3 hours to obtain Compound 110 shown in Table 1. The reaction product (crude yield : 80%) was then purified by distilling off the solvent and by subsequent preparative liquid chromatography conducted under the same conditions as described in Example A to remove unreacted materials and by-products. Thus 19.8 g. of purified Compound 110 having the following analyses was obtained.

Elemental analysis (unit : %)

|   | Measured value | Calculated value |
| --- | --- | --- |
| C | 53.2 | 53.0 |
| H | 7.5 | 7.7 |
| O | 26.3 | 26.5 |
| Na | 12.9 | 12.7 |

MMR ($D_2O$) : δ0.86 (bt, 3H), 1.28 (bs, 16H), 1.38–1.69 (m,2H), 3.40–3.70 (m, 3H), 3.72–4.08 (m, 4H)

IR (KBr) : $cm^{-1}$ 3430, 2955, 2925, 2850, 1610, 1465, 1425, 1320, 1090, 1070, 720

Weak acid value (mg.KOH/g.) : 311.0 (calculated value : 309.9)

CMC (mol./l.) : $4.5 \times 10^{31}$ 3

EXAMPLE E

Into a 1 liter four-necked flask were weighed 50.0 g. of 1,2-tetradecanediol, 250 g. of dioxane and 10.0 g. of metallic sodium, and the mixture was heated to 100° C. under a nitrogen atmosphere. The mixture was stirred and maintained at 100° C. for 5 hours to complete the alkoxidation, then cooled to 70° C. Then 55.6 g. of sodium monochloroacetate was gradually added thereto. After completion of the addition, the reaction was continued at 70° C. for 3 hours to obtain Compound 111 shown in Table 1. The reaction product (crude yield : 75%) was then purified by distilling off the solvent and by subsequent preparative liquid chromatography conducted under the same conditions as described in Example A to remove unreacted materials and by-products. Thus 18.2 g. of purified Compound 111 having the following analyses was obtained.

Elemental analysis (unit : %)

|   | Measured value | Calculated value |
|---|---|---|
| C | 55.3 | 55.4 |
| H | 8.1 | 8.2 |
| O | 24.7 | 24.6 |
| Na | 11.9 | 11.7 |

MMR ($D_2$ O) : $\delta$0.87 (bt, 3H), 1.29 (bs, 20H), 1.37–1.64 (m, 2H), 3.42–3.72 (m, 3H), 3.72–4.08 (m, 4H)

IR (KBr) : $cm^{-1}$ 3450, 2955, 2925, 2850, 1610, 1465, 1455, 1425, 1375, 1325, 1090, 1070, 720

Weak acid value (mg.KOH/g.) : 289.0 (calculated value : 287.7)

EXAMPLE F 5.0 g. of the sodium hydroxyether monocarboxylate obtained in Example D was dissolved in 50 g. of water. After acidifying the solution with hydrochloric acid, the solute was extracted with ether. Thus 4.6 g. of the purified hydroxyether monocarboxylic acid having the following analyses was obtained.

Elemental analysis (unit : %)

|   | Measured value | Calculated value |
|---|---|---|
| C | 62.2 | 62.4 |
| H | 9.8 | 9.8 |
| O | 27.9 | 27.7 |

Acid value (mg.KOH/g.) : 324.1 (calculated value : 324.3)

COMPARATIVE EXPERIMENT

For purposes of comparison, surfactants obtained in Examples 1, 4, A and D; sodium poly(oxyethylene)-laurylether carboxylate [$C_{12}H_{25}O(CH_2CH_2O)_2CH_2$——COONa], Comparative Example 1; sodium laurate, Comparative Example 2; and sodium dodecenyl succinate, Comparative Example 3, were tested for foaming power, ability to reduce surface tension and irritation to the skin. The results are reported in FIG. 1 and A, in Table 1 and 2 as well. From these results it is seen that the compounds of the present invention are more effective as surfactant in the pH range of from weak acid to alkali, besides being less irritative to the skin.

FOAMING POWER 200 ml. of 0.30% aqueous solution was prepared for each sample using a hard water having a hardness of 15 ppm (as CaO), then the solution was subjected to agitation for 30 seconds at 30° C. in a juicer-mixer (MX-390GN made by Toshiba). Foaming power was determined by the height of foam (mm.) at the end of 30 seconds' agitation.

ABILITY TO REDUCE SURFACE TENSION

Surface tension was measured at 30° C. for each 0.30% aqueous solution, with a surface tension meter of Wilhelm type (made by Kyowa Kagaku), to compare ability of each sample to reduce surface tension.

SKIN IRRITATION 1.0% aqueous solution was prepared for each sample, then a closed patch test (for 48 hours, at the inside upper arms) was carried out by a group of subjects (five men and five women). The degree of skin irritation was judges according to the following criterion:

CRITERION FOR JUDGEMENT

0 : no reaction (no erythema) observed
1 : slight erythema
2 : clear erythema
3 : medium or intensive erythema
4 : fleshlike red erythema

TABLE 2

|  | Surface Tension (dyne/cm.) | | | |
|---|---|---|---|---|
|  | pH 5.5 | pH 7.0 | pH 8.5 | pH 10.0 |
| Example 1 | 22.7 | 23.0 | 23.2 | 23.2 |
| Example 4 | 23.0 | 24.0 | 25.5 | 27.0 |
| Example A | 24.0 | 24.0 | 26.0 | 26.3 |
| Example D | 23.0 | 24.0 | 25.5 | 27.0 |
| Comparative Example 1 | — | 32.0 | 33.0 | — |
| Comparative Example 2 | * | * | 29.8 | 32.0 |
| Comparative Example 3 | * | 27.3 | 27.4 | 31.1 |

*Samples were insoluble in water so that the measurement could not be done.

TABLE 3

|  | Skin Irritation |
|---|---|
| Example 1 | 2 |
| Example 4 | 2 |
| Example A | 2 |
| Example D | 2 |
| Comparative Example 1 | 6 |
| Comparative Example 2 | 8 |
| Comparative Example 3 | 35 |

Figure 2:
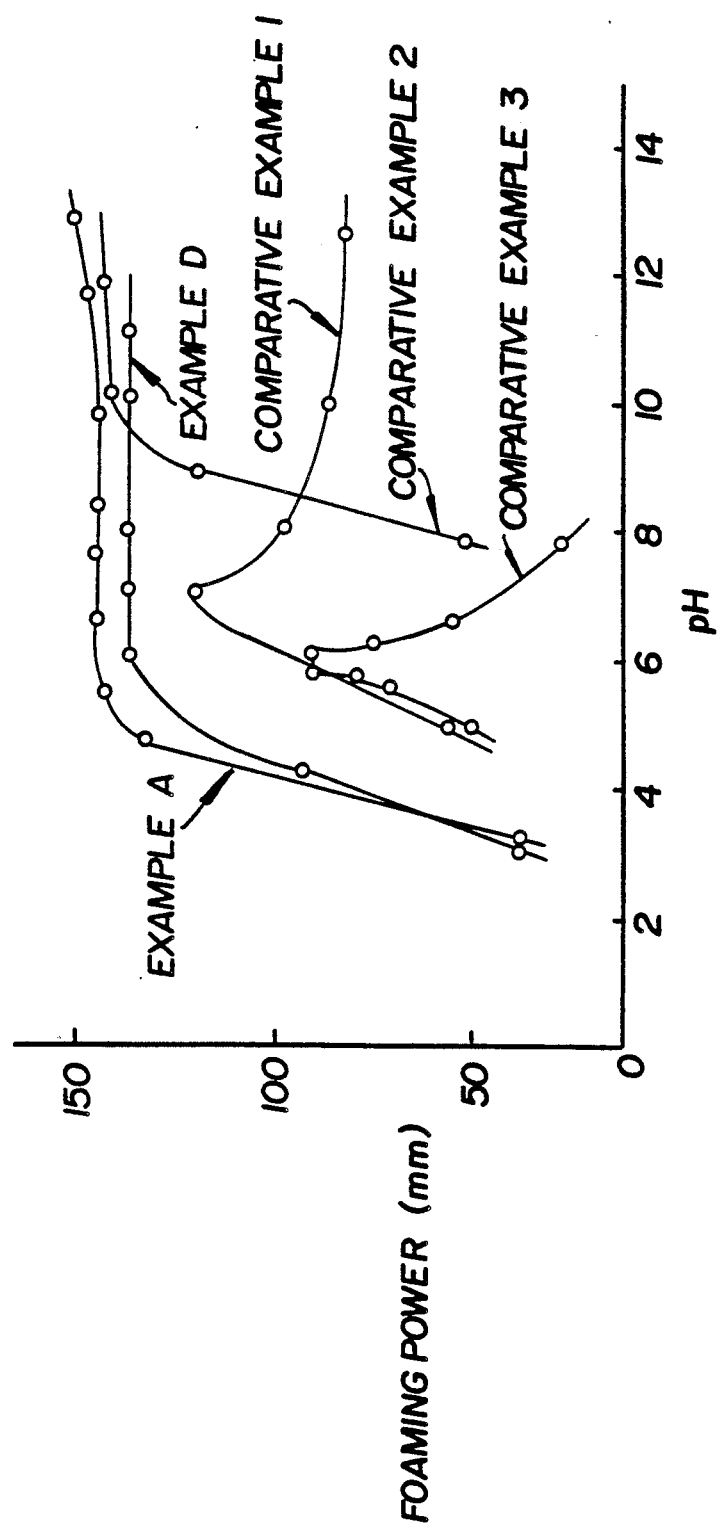

Brief explanation on the drawings:

FIG. 1 and 2 show the relationship between foaming power and pH of the solution.

What is claimed is:

1. Carboxylic acids represented by the general formula:

$$RCHCH_2OX_1 \atop OX_2 \qquad (I)$$

wherein R is a linear or granched alkyl or alkenyl group containing from 8 to 16 carbon atoms; one of $X_1$ and $X_2$ is a —$(CH_2)_n$—COOM group, and the other is a hydrogen atom; M is a hydrogen atom, an alkali metal, an alkaline earth metal, ammonium, a lower alkanol amine cation, a lower alkylamine cation or a basic amino acid cation; and n is 1 or 2.

2. A mixture of at least one of the carboxylic acids of claim 1 with at least one dicarboxylic acid of the same general formula, wherein $X_1$ and $X_2$ are both —$(CH_2)_n$—COOM groups, in a weight ratio of 9:1 to 2:8.

3. A process for producing carboxylic acids represented by the general formula:

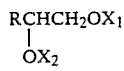  (1)

wherein R is a linear or branched alikyl or alkenyl group containing from 4 to 34 carbon atoms; one or both of $X_1$ and $X_2$ are $-(CH_2)_n-COOM$ groups, any other is a hydrogen atom; M is a hydrogen atom, an alkali metal, an alkaline earth metal, ammonium, a lower alkanol amine cation, a lower alkylamine cation or a basic amino acid cation; and n is 1 or 2; comprising a carboxymethylation of the ester of a 1,2-epoxyalakane represented by the general formula:

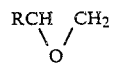  (3)

wherein R is a linear or branched alkyl or alkenyl group having from 4 to 34 carbon atoms; with a monohaloacetic acied and/or its salt in the presence of an alkali.

* * * * *